United States Patent [19]

Bolich, Jr. et al.

[11] Patent Number: 4,788,006

[45] Date of Patent: Nov. 29, 1988

[54] SHAMPOO COMPOSITIONS CONTAINING NONVOLATILE SILICONE AND XANTHAN GUM

[75] Inventors: Raymond E. Bolich, Jr., Maineville; Theresa B. Williams, Cincinnati, both of Ohio

[73] Assignee: The Procter & Gamble Company, Cincinnati, Ohio

[21] Appl. No.: 824,034

[22] Filed: Jan. 30, 1986

Related U.S. Application Data

[63] Continuation-in-part of Ser. No. 694,870, Jan. 25, 1985, abandoned.

[51] Int. Cl.⁴ .................... C11D 1/14; C11D 3/22
[52] U.S. Cl. .................. 252/550; 252/174.15; 252/174.17; 252/551; 252/554; 252/555; 252/DIG. 2; 252/DIG. 13
[58] Field of Search ............ 252/174.15, 174.17, 252/174.18, 550, 551, 554, 555, 558, DIG. 2, DIG. 13, DIG. 14

[56] References Cited

U.S. PATENT DOCUMENTS

| | | | |
|---|---|---|---|
| 3,957,970 | 5/1976 | Korkis | 424/70 |
| 3,964,500 | 6/1976 | Drakoff | 252/542 |
| 4,061,585 | 12/1977 | Finn et al. | 252/89 |
| 4,278,657 | 7/1981 | Tezuka et al. | 424/63 |
| 4,341,799 | 7/1982 | Good | 424/365 |
| 4,364,837 | 12/1982 | Pader | 252/173 |
| 4,390,451 | 6/1983 | Havinga et al. | 252/311 |
| 4,465,619 | 8/1984 | Boskamp | 252/540 |
| 4,479,893 | 10/1984 | Hirota et al. | 252/542 |
| 4,704,272 | 11/1987 | Oh et al. | 424/70 |
| 4,728,457 | 3/1988 | Fieler et al. | 252/174.15 |

FOREIGN PATENT DOCUMENTS

| | | |
|---|---|---|
| 849433 | 9/1960 | United Kingdom . |
| 1034782 | 7/1966 | United Kingdom . |
| 2103230 | 2/1983 | United Kingdom . |

OTHER PUBLICATIONS

Kelco, "Xanthan Gum," Merck & Co.
Hennock, M. et al., "Effect of Xanthan Gum Upon the Rheology and Stability of Oil-Water Emulsions", Journal of Food Science, vol. 49 (1984) pp. 1271–1279.

*Primary Examiner*—Prince E. Willis
*Attorney, Agent, or Firm*—Richard C. Witte; John V. Gorman; Douglas C. Mohl

[57] ABSTRACT

Shampoos are disclosed which comprise a synthetic, anionic surfactant, a dispersed, insoluble, non-volatile silicone, a xanthan gum suspending agent and water.

17 Claims, No Drawings

SHAMPOO COMPOSITIONS CONTAINING NONVOLATILE SILICONE AND XANTHAN GUM

CROSS REFERENCE TO RELATED APPLICATION

This is a continuation-in-part of application Ser. No. 694,870, filed on Jan. 25, 1985, now abandoned.

TECHNICAL FIELD

The present invention is related to conditioning shampoos which have a dispersed, insoluble, non-volatile silicone phase and are stabilized through the use of xanthan gum.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. A variety of approaches have been developed to alleviate the after-shampoo problems. These range from the inclusion of hair conditioning aids in shampoos to post-shampoo application of hair conditioners, i.e., hair rinses. Hair rinses typically work by depositing a polymeric film or other material onto the hair. However, such solutions to a very prevalent problem have not been fully satisfactory. For one thing, hair rinses are generally liquid in nature and must be applied in a separate step following the shampooing, left on the hair for a length of time, and rinsed with fresh water. This, of course, is time consuming and is not convenient.

While shampoos have been disclosed which contain conditioning aids, they have not been totally satisfactory for a variety of reasons. One problem relates to compatibility problems between good cleaning anionic surfactants and the fatty cationic agents which are good conditioning agents. This has caused other surfactants such as nonionics, amphoterics and zwitterionics to be examined by workers in the field. Many of these efforts are reflected in patents issued in the conditioning shampoo area. See for example U.S. Pat. No. 3,849,348, Nov. 19, 1974 to Hewitt; U.S. Pat. No. 3,990,991, Nov. 9, 1961 to Gerstein; and U.S. Pat. No. 3,822,312, July 2, 1974 to Sato.

The use of these other surfactants solved many of the compatibility problems but still did not provide complete answers in all areas. For instance cationic conditioners may not deliver the desired level of softness desired by users. Materials which can provide increased softness are silicones, both those which are soluble as well as insoluble in the shampoo matrix.

Silicones in shampoo compositions have been disclosed in a number of different publications. Such publications include U.S. Pat. No. 2,826,551, Mar. 11, 1958 to Geen; U.S. Pat. No. 3,964,500, June 22, 1976 to Drakoff; U.S. Pat. No. 4,364,837, Dec. 21, 1982 to Pader; British Pat. No. 849,433, Sept. 28, 1960 to Woolston; U.S. Pat. No. 4,341,799, July 27, 1982 to Good, and U.S. Pat. No. 4,465,619, Aug. 14, 1984 to Boskamp. While these patents disclose silicone containing compositions, they also do not provide answers to all of the problems encountered in making a totally satisfactory product. One unsolved problem is that of keeping a dispersed, insoluble, non-volatile silicone material suspended and the total product stable while still providing satisfactory shampoo performance. A variety of materials have been included in silicone containing shampoos for purposes of thickening and stabilization but totally satisfactory solutions are lacking. It has been surprisingly found that compositions comprising specific components can provide stable compositions without interfering unduly with the deposit of the silicone material onto the hair and other shampoo functions.

It is an object of the present invention to provide a stable silicone containing conditioning shampoo.

It is a further object of the present invention to provide silicone shampoo compositions containing xanthan gum.

It is a further object of the present invention to provide shampoos which provide good conditioning (e.g., ease of combing, softness, feel, etc.) to hair.

It is a further object of the present invention to provide an improved method of shampooing and conditioning hair.

These and other objects will become readily apparent from the detailed description which follows.

Unless otherwise indicated, all percentages and ratios herein are by weight.

SUMMARY OF THE INVENTION

The present invention relates to shampoo compositions comprising from about 5% to about 50% of a synthetic anionic surfactant, about 0.1% to about 10.0% of an insoluble, non-volatile, dispersed silicone, about 0.3% to about 5% of xanthan gum and water. These as well as optional components are described in detail below.

DETAILED DESCRIPTION

The essential and optional components of the present invention are given in the following paragraphs.

Surfactant

An essential component of the present compositions is a synthetic, anionic surfactant. The surfactant is present at a level of from about 5% to about 50%, preferably from about 10% to about 30%, most preferably from about 12% to about 25%.

Synthetic anionic detergents useful herein include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulphates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight $C_{12-13}$ compounds; from 60 to 100% by weight of $C_{14-15-16}$ compounds, from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Additional examples of anionic synthetic detergents which come within the terms of the present invention are the reaction product of fatty acids esterified with isethionic acid and neutralized with sodium hydroxide where, for example, the fatty acids are derived from coconut oil; sodium or potassium salts of fatty acid amides of methyl tauride in which the fatty acids, or example, are derived from coconut oil. Other anionic synthetic detergents of this variety are set forth in U.S. Pat. Nos. 2,486,921; 2,486,922; and 2,396,278.

Still other anionic synthetic detergents include the class designated as succinamates. This class includes such surface active agents as disodium N-octadecylsulfosuccinamate; tetrasodium N-(1,2-dicarboxyethyl)-N-octadecylsulfo-succinamate; diamyl ester of sodium sulfosuccinic acid; dihexyl ester of sodium sulfosuccinic acid; dioctyl esters of sodium sulfosuccinic acid.

Other suitable anionic detergents utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880 of Phillip F. Pflaumer and Adrian Kessler, issued July 25, 1967, titled "Detergent Composition", the disclosure of which is incorporated herein by reference.

Another class of anionic organic detergents are the β-alkyloxy alkane sulfonates. These compounds have the following formula:

$$R_1-\underset{\underset{H}{|}}{\overset{\overset{OR_2}{|}}{C}}-\underset{\underset{H}{|}}{\overset{\overset{H}{|}}{C}}-SO_3M$$

where $R_1$ is a straight chain alkyl group having from 6 to 20 carbon atoms, $R_2$ is a lower alkyl group having from 1 (preferred) to 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein to provide superior cleaning levels under household washing conditions include:

potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium β-methoxyoctadecylsulfonate, and ammonium β-n-propoxydodecylsulfonate.

Many additional nonsoap synthetic anionic surfactants are described in McCUTCHEON'S DETERGENTS AND EMULSIFIERS, 1984 ANNUAL, published by Allured Publishing Corporation, which is incorporated herein by reference. Also U.S. Pat. No. 3,929,678, Dec. 30, 1975 to Laughlin et al. discloses many other anionic as well as other surfactant types and is incorporated herein by reference.

The above-mentioned surfactants can be used alone or in combination in the shampoo compositions of the present invention. The alkyl sulfates, the ethoxylated alkyl sulfates and mixtures thereof are preferred for use herein.

Non-Volatile Silicone Fluid

The non-volatile silicone fluid may be either a polyalkyl siloxane, a polyaryl siloxane, a polyalkylaryl siloxane or a polyether siloxane copolymer and is present at a level of from about 0.1% to about 10.00% preferably from about 0.5% to about 5.0%. Mixtures of these fluids may also be used and are preferred in certain executions. Additionally volatile silicones, as is noted below, may be used as part of the silicone mixture so long as the final mixture is non-volatile. The dispersed silicone particles should also be insoluble in the shampoo matrix. This is the meaning of "insoluble" as used hereinbefore and hereinafter.

The essentially non-volatile polyalkyl siloxanes that may be used include, for example, polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, July 20, 1970. Preferably the viscosity ranges from about 350 centistokes to about 100,000 centistokes.

The essentially non-volatile polyalkylaryl siloxanes that may be used include, for example, polymethylphenylsiloxanes having viscosities of about 15 to 65 centistokes at 25° C. These siloxanes are available, for example, from the General Electric Company as SF 1075 methyl phenyl fluid or from Dow Corning as 556 Cosmetic Grade Fluid. Additionally poly(dimethyl siloxane) (diphenyl siloxane) copolymers having a viscosity in the range of from about 10 to about 100,000 centistokes at 25° C. are useful.

The essentially non-volatile polyether siloxane copolymer that may be used is, for example, a polypropylene oxide modified dimethylpolysiloxane (e.g., Dow Dorning DC-1248) although ethylene oxide or mixtures of ethylene oxide and propylene oxide may also be used.

References disclosing suitable silicones include the previously mentioned U.S. Pat. No. 2,826,551 to Geen, U.S. Pat. No. 3,964,500, June 22, 1967 to Drakoff; U.S. Pat. No. 4,364,837 to Pader and British Pat. No. 849,433 to Woolston. All of these patents are incorporated herein by reference. Also incorporated herein by reference is *Silicon Compounds* distributed by Petrarch Systems, Inc., 1984. This reference provides a very good listing of suitable silicone materials.

Another silicone material found especially useful in the present compositions to provide good dry combing is a silicone gum. Silicone gums described by Petrarch and others including U.S. Pat. No. 4,152,416, May 1, 1979 to Spitzer et al. and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference. "Silicone gum" materials denote high molecular weight polydiorganosiloxanes generally having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof. The gums may contain some minor (e.g., 6% to 14% of the total gum weight) of a cyclic volatile silicone.

Xanthan Gum

Xanthan gum is the agent used in the present compositions to suspend the silicone fluid. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. This information and other is found in Whistler, Roy L. Editor *Industrial Gums—Polysaccharides and Their Derivatives* New York: Academic Press, 1973. Kelco, a Division of Merck & Co., Inc. offers xanthan gum as Keltrol ®. The gum is present at a level of from about 0.3% to about 3%, preferably from about 0.4% to about 1.2% in the compositions of the present invention.

Water

Water is the last essential component of the present invention and forms the remainder of the composition. It is generally present at a level of from about 20% to about 95%, preferably from about 60% to about 85%.

Optional Components

The shampoos herein can contain a variety of nonessential optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea; cationic surfactants such as, tricetyl methyl ammonium chloride, cetyl trimethyl ammonium chloride, stearyldimethyl benzyl ammonium chloride, and di(partially hydrogenated tallow) dimethylammonium chloride; thickeners and viscosity modifiers such as a diethanolamide of a long chain fatty acid (e.g., PEG 3 lauramide), cocomonoethanol amide, amine oxides, block polymers of ethylene oxide and propylene oxide such as Pluronic F88 offered by BASF Wyandotte, fatty alcohols such as cetearyl alcohol, sodium chloride, sodium sulfate, polyvinyl alcohol, and ethyl alcohol; pH adjusting agents such as citric acid, sodium citrate, succinic acid, phosphoric acid, sodium hydroxide, sodium carbonate, etc.; perfumes; dyes; and, sequestering agents such as disodium ethylenediamine tetraacetate. Such agents generally are used individually at a level of from about 0.01% to about 10%, preferably from about 0.5% to about 5.0% by weight of the composition.

Another optional ingredient and one preferred for use in certain of the compositions of this invention, is a volatile silicone or a water insoluble hydrocarbon. These agents are disclosed in U.S. Pat. No. 4,472,375, Sept. 18, 1984 to R. E. Bolich, Jr. incorporated herein by reference. These agents help disperse the higher molecular weight, non-volatile silicones in the product when the product is used. These agents are used at levels from about 0.1% to about 5%.

The pH of the present compositions is not critical and may be in the range of from 4 to about 10.

As with all compositions, the present compositions should not contain components which unduly interfere with the performance of the compositions. In this regard, the present compositions should preferably contain less than about 10% of a water-soluble polysaccharide.

METHOD OF MANUFACTURE

The shampoos of the present invention can be made in the following manner:

(A) Mix the water and surfactant of the composition together using a turbine blade at 500 r.p.m.

(B) Heat the mixture of (A) to 66° C., increase the agitation sufficient to create a vortex and disperse the xanthan gum in the vortex created. During this step the temperature is kept at about 66° C.

(C) Add the remaining ingredients (except for the silicone) while agitating at the same speed.

(D) Add the silicone and shear the composition with a high shear mixer until the silicone particles are on average 10 microns in diameter (the particle size distribution may be from about 2 to about 55 microns).

(E) Cool the composition to 27° C. while mixing at 500 r.p.m.

INDUSTRIAL APPLICABILITY

The present compositions are used in a conventional manner for cleaning hair. From about 0.1 g to about 10 g of a composition is applied to hair that has been wetted, generally with water, worked through the hair and then rinsed out.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLES I-V

The following compositions are representative of the present invention.

| Component | Weight % | | | | |
|---|---|---|---|---|---|
| | I | II | III | IV | V |
| $NH_4 C_{12-14}$ Alkyl Sulfate | — | 16.00 | 8.00 | 16.00 | 8.00 |
| $NH_4 C_{12-14}$ Alkyl (Ethoxy) Sulfate | — | — | 8.00 | — | 8.00 |
| TEA $C_{12-14}$ Alkyl Sulfate | 18.20 | — | — | — | — |
| Xanthan Gum | 0.75 | 0.75 | 0.40 | 2.00 | 0.75 |
| Cocamide MEA | 3.00 | 1.00 | 3.00 | 1.50 | 1.00 |
| 50% Caustic Soda | 0.60 | 0.01 | — | — | 0.01 |
| Citric Acid | — | — | 0.60 | — | — |
| Sodium Chloride | 1.00 | 0.12 | 1.50 | — | — |
| DC-200 (12,500 csk)[1] | 5.00 | — | 3.00 | — | — |
| DC-200 (350 csk)[2] | — | 1.00 | — | — | 2.00 |
| DC-200 (600,000 csk)[3] | — | — | — | 3.00 | — |
| Dye Solution | 0.15 | 0.65 | 0.15 | — | 0.65 |
| Ethylene glycol distearate | — | 0.75 | — | — | 0.75 |
| Preservative | 0.033 | 0.033 | 0.033 | — | 0.033 |
| Cetearyl Alcohol | — | 1.00 | — | — | 1.00 |
| Perfume | 0.60 | 1.00 | 0.60 | 0.50 | 1.00 |
| Silicone Gum[4] | — | 1.00 | — | — | 1.00 |
| Water (Double Reverse Osmosis) | qs 100% | → | → | → | → |

[1]Dimethylpolysiloxane offered by Dow Corning Corporation
[2]Dimethylpolysiloxane offered by Dow Corning Corporation
[3]Dimethylpolysiloxane offered by Dow Corning Corporation
[4]Dimethylpolysiloxane gum offered by General Electric Company as Silicone Compound SE-76

The above compositions are stable and deliver good conditioning to hair that is washed with them. If in the compositions other anionic surfactants such as alpha olefin sulfonates or alkyl glyceryl sulfonates, are used in place of those listed, similar results are obtained. Similarly if silicones of other viscosities and types, such as those listed on pages 6-8, are used in place of those listed, similar results are obtained.

What is claimed is:
1. A shampoo composition consisting essentially of:
   (a) from about 5% to about 50% of synthetic anionic surfactant or mixtures thereof;
   (b) from about 0.1% to about 10% of a dispersed, insoluble, nonvolatile silicone or mixtures thereof;
   (c) from about 0.4% to about 5% of xanthan gum; and
   (d) the remainder water.
2. A shampoo composition according to claim 1 wherein the surfactant is selected from the group consisting of alkyl sulfates, ethoxylated alkyl sulfates, alpha olefin sulfonates, alkyl sulfonates and mixtures thereof.
3. A shampoo composition according to claim 2 wherein the non-volatile silicone has viscosity of from about 5 to about 600,000 centistokes at 25° C.
4. A shampoo composition according to claim 3 wherein the surfactant is selected from the group consisting of alkyl sulfates, ethoxylated alkyl sulfates and mixtures thereof.
5. A shampoo composition according to claim 4 wherein the non-volatile silicone is a polydimethylsiloxane.
6. A shampoo composition according to claim 5 wherein an amide is also present in the compositions.
7. A shampoo composition according to claim 6 wherein the surfactant is an alkyl sulfate.
8. A shampoo composition according to claim 7 wherein the polydimethylsiloxane has a viscosity of 350 centistokes at 25° C.
9. A shampoo composition according to claim 8 wherein the surfactant is ammonium alkyl sulfate.
10. A shampoo composition according to claim 1 wherein the non-volatile silicone composition is a mixture of non-volatile silicones.
11. A shampoo composition according to claim 10 wherein one of the non-volatile silicones is a silicone gum.
12. A shampoo composition according to claim 11 which additionally contains a volatile silicone.
13. A method of shampooing hair comprising applying from about 0.1 g to about 10 g of a composition according to claim 1 to hair that has been wet with water and then rinsed out.
14. A method according to claim 13 wherein the composition is in accordance with claim 4.
15. A method according to claim 13 wherein the composition is in accordance with claim 10.
16. A method according to claim 13 wherein the composition is in accordance with claim 11.
17. A method according to claim 13 wherein the composition is in accordance with claim 12.

* * * * *